United States Patent [19]

Maxey

[11] 4,352,760

[45] Oct. 5, 1982

[54] ORGANIC COMPOUNDS SUBSTITUTED HEPTADECA-5,9- AND 5,10-DIENOIC ACID

[75] Inventor: Kirk M. Maxey, Kalamazoo, Mich.

[73] Assignee: The Upjohn Company, Kalamazoo, Mich.

[21] Appl. No.: 220,598

[22] Filed: Dec. 29, 1980

[51] Int. Cl.$^3$ ............................................. C07C 57/02
[52] U.S. Cl. .................................. 260/404; 564/156; 564/160; 260/239 B; 564/340; 564/347; 260/326.5 E; 564/366; 564/383; 260/326.43; 564/503; 564/509; 260/404.5; 560/60; 560/83; 260/408; 560/105; 560/111; 260/413; 560/112; 560/113; 260/465 E; 562/470; 562/586; 260/465.6; 562/587; 564/170; 260/465.5 R; 564/175; 564/176; 542/416; 564/150; 564/151; 542/421; 564/155; 564/158; 542/427; 564/159; 564/148; 542/438; 564/149; 564/310; 544/175; 260/239; 546/237; 546/340; 546/265; 568/648; 568/649; 568/654; 568/673; 568/674; 564/87; 564/89; 564/91; 564/92; 564/93; 564/95; 564/97; 564/98; 564/313; 564/99

[58] Field of Search ............. 260/404, 404.5, 408 CN, 260/408 F, 408 R, 410.9 Q, 413, 413 K, 413 R, 465 F, 465 P, 465.6, 465.5 R, 239 B, 239 BF, 326.5 E, 326.43; 562/470, 586, 587, 105, 111, 112, 113; 560/60, 183, 105, 111, 112, 113; 564/170, 175, 176, 150, 151, 155, 158, 159, 148, 149, 310, 313, 87, 89, 91, 92, 93, 95, 97, 98, 99, 156, 160, 346, 347, 366, 383, 503, 509; 568/648, 649, 654, 673, 674; 542/416, 421, 427, 438; 546/237, 340, 265, 389; 544/175

[56] References Cited

U.S. PATENT DOCUMENTS 4,097,504  6/1978  Cragoe et al. ...................... 260/404
4,112,224  9/1978  Bundy .

OTHER PUBLICATIONS

Harris et al., Adv. in Prostaglandin and Thromboxane Research 6:437 (1980).
Miyamoto et al., Adv. in Prostaglandin and Thromboxane Research 6:443 (1980).

Primary Examiner—Arthur P. Demers
Attorney, Agent, or Firm—Lawrence T. Welch

[57] ABSTRACT

The present invention provides novel substituted heptadeca-5,9- and 5,10-dienoic acid and similar fatty acid compounds which are derivatives of certain prostaglandins and are potent thromboxane $A_2$ inhibitors. By virtue of this pharmacological property, they represent useful pharmacological agents for a wide variety of purposes.

27 Claims, No Drawings

ORGANIC COMPOUNDS SUBSTITUTED HEPTADECA-5,9- AND 5,10-DIENOIC ACID

DESCRIPTION

1. BACKGROUND OF THE INVENTION

The present invention relates to novel compositions of matter. More particularly the present invention relates to novel derivatives of PGF-type compounds. Most particularly the present invention relates to substituted heptadeca-5,9- and 5,10-dienoic acid and similar long chain fatty acid prostaglandin derivatives.

The prostaglandins are a family of 20 carbon atom fatty acids being structural derivatives of prostanoic acid, which exhibit useful activity in a wide variety of biological systems. Accordingly, such prostaglandins represent useful pharmacological agents in the treatment and prevention of a wide variety of disease conditions. For a fuller discussion of prostaglandins, see Bergstrom, et al., Pharmacol. Rev. 20:1 (1968) and references cited therein.

The compounds of the present invention are derived from prostaglandin $F_2\alpha$ ($PGF_2\alpha$) and its analogs. $PGF_2\alpha$ has the structure and carbon atom numbering as shown in formula I. When $PGF_2\alpha$ is used as the starting material, the compounds of the present invention which are derived therefrom are named as heptadecadienoic acids, and this name will be used throughout to refer to these compounds. However, when a prostaglandin analog of varying chain length (i.e., other than 20 carbon atoms) is used, a different fatty acid derivative is formed.

The compounds of the present invention are potent thromboxane $A_2$ inhibitors and as such represent useful pharmacological agents. For a discussion of thromboxane $A_2$ inhibition and its benefits, see, e.g., Gorman, Adv. in Prostaglandin and Thromboxane Research 6:417 (1980), and references cited therein.

2. PRIOR ART

A number of thromboxane inhibitors are known; e.g., biheterocyclic 9,11-trideoxy-PGF compounds disclosed in U.S. Pat. No. 4,112,224; SQ 80,388 (1-(3-phenyl-2-propenyl)-1H-imidazole) disclosed in Harris, et al., Adv. in Prostaglandin and Thromboxane Research 6:437 (1980); and pyridine and its derivatives, disclosed in Miyamoto, et al., Adv. in Prostaglandin and Thromboxane Research 6:443 (1980).

SUMMARY OF THE INVENTION

The present invention particularly provides a compound of the formula II or III,
wherein $P_1$ is
 (a) $-C(OH)(H)-CH_2-C(H)=CH_2$;
 (b) $-C(OH)(H)-CH_2-C\equiv N$;
 (c) $-C(OH)(H)-C(=CH_2)C(O)H$; or
 (d) $-C(OH)H-C(=CH_2)C\equiv N$;
wherein $R_{67}$ is hydroxy, chloro, bromo, or fluoro;
wherein $X_1$ is
 (a) $-CO_2R_1$, wherein $R_1$ is hydrogen, alkyl of from one to 12 carbon atoms, cycloalkyl of 3 to 10 carbon atoms, aralkyl of from 7 to 12 carbon atoms, phenyl, phenyl substituted by one, 2 or 3 chloro or one, 2 or 3 alkyl, or phenyl substituted in the para position by
  (i) $NHC(O)R_{25}$
  (ii) $-O-C(O)R_{26}$,
  (iii) $-CO_2R_1$
  (iv) $-O-C(O)-(p-Ph)-R_{27}$, wherein p-Ph is 1,4-phenylene, or
  (v) $-CH=N-NH-C(O)-NH_2$;
  wherein $R_{25}$ is methyl, phenyl, acetamidophenyl, benzoylamidophenyl, or $NH_2$; wherein $R_{26}$ is methyl, phenyl, $NH_2$, or methoxy; wherein $R_{27}$ is hydrogen, acetamido, benzoylamido; or $R_1$ can be a pharmacologically acceptable cation;
 (b) $-COW_1$, wherein $W_1$ is
  (i) amido of the formula $-NR_{21}R_{22}$, wherein $R_{21}$ and $R_{22}$ are the same or different and are: hydrogen;
   alkyl of one to 12 carbon atoms, inclusive;
   cycloalkyl of 3 to 10 carbon atoms, inclusive;
   aralkyl of 7 to 12 carbon atoms, inclusive;
   phenyl;
   phenyl substituted with one, 2, or 3 chloro, alkyl of one to 3 carbon atoms, inclusive, hydroxy, carboxy, alkoxycarbonyl of one to 4 carbon atoms, inclusive, or nitro;
   carboxyalkyl of one to four carbon atoms, inclusive;
   carbamoylalkyl of one to 4 carbon atoms, inclusive;
   cyanoalkyl of one to 4 carbon atoms, inclusive;
   acetylalkyl of one to 4 carbon atoms, inclusive;
   benzoylalkyl of one to 4 carbon atoms, inclusive;
   benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
   pyridyl;
   pyridyl substituted by one, 2, or 3 chloro, alkyl of one to 3 carbon atoms, inclusive, or alkoxy of one to 3 carbon atoms, inclusive;
   pyridylalkyl of one to 4 carbon atoms, inclusive; or
   pyridylalkyl substituted by one, 2, or 3 chloro, alkyl of one to 3 carbon atoms, inclusive, hydroxy, alkoxy of one to 3 carbon atoms, inclusive, hydroxyalkyl of one to 4 carbon atoms, inclusive, dihydroxyalkyl of one to 4 carbon atoms inclusive, or trihydroxyalkyl of one to 4 carbon atoms, inclusive;
   with the further proviso that not more than one of $R_{21}$ and $R_{22}$ is other than hydrogen or alkyl;
  (ii) cycloamido selected from the group consisting of
   1-pyrrolidinyl,
   1-piperidinyl,
   4-morpholinyl,
   hexahydro-1H-azepin-1-yl,
   3-pyrrolin-1-yl, or
   3,6-dihydro-1(2H)-pyridinyl, substituted by $R_{21}$ or $R_{22}$ or both or
   1-piperazinyl substituted at the 4 position by $R_{21}$, wherein $R_{21}$ and $R_{22}$ are as defined above;
  (iii) carbonylamido of the formula $-NR_{23}COR_{21}$, wherein $R_{23}$ is hydrogen or alkyl of one to 4 carbon atoms and $R_{21}$ is as defined above;
  (iv) sulfonylamido of the formula $-NR_{23}SO_2R_{21}$, wherein $R_{21}$ and $R_{23}$ are as defined above; or
  (v) hydrazino of the formula $-NR_{23}R_{24}$, wherein $R_{24}$ is amido of the formula $-NR_{21}R_{22}$, as defined above, or cycloamido, as defined above;
 (c) $CH_2OH$;

(d) CH$_2$NR$_{31}$R$_{32}$, wherein R$_{31}$ and R$_{32}$ are the same or different and are hydrogen or alkyl of from one to 4 carbon atoms;

wherein Z$_1$ is
- (a) cis—CH=CH—CH$_2$(CH$_2$)$_g$—CH$_2$—;
- (b) trans—CH=CH—CH$_2$(CH$_2$)$_g$—CH$_2$;
- (c) —CH=CH—CH$_2$(CH$_2$)$_g$CF$_2$—;
- (d) trans—CH=CH—CH$_2$(CH$_2$)$_g$—CH$_2$—;
- (e) cis—CH$_2$—CH=CH—(CH$_2$)$_g$—CH$_2$;
- (f) trans—CH$_2$—CH=CH—(CH$_2$)$_g$—CH$_2$;
- (g) —(CH$_2$)$_3$—(CH$_2$)$_g$—CH$_2$;
- (h) —(CH$_2$)$_3$—(CH$_2$)$_g$—CF$_2$;
- (i) —CH$_2$—O—CH$_2$—(CH$_2$)$_g$—CH$_2$—;
- (j) phenyl substituted by —CH$_2$(CH$_2$)$_g$ or —O—(CH$_2$)$_g$, wherein g is one, 2, or three;

wherein L$_1$ is $\alpha$—R$_3$:$\beta$—R$_4$ or $\beta$—R$_3$:$\alpha$—R$_4$ or a mixture of the two, wherein R$_3$ and R$_4$ are the same or different and are hydrogen, methyl, or fluoro, with the proviso that when R$_3$ is fluoro R$_4$ is fluoro and when R$_4$ is fluoro R$_3$ is fluoro;

wherein R$_7$ is
- (a) —(CH$_2$)$_m$—CH$_3$;
- (b) O—(Ph—s); or
- (c) —(CH$_2$)$_n$(Ph—s); wherein (Ph—s) is phenyl or phenyl substituted by zero, one, 2, or 3 chloro, fluoro, trifluoromethyl, alkyl of from one to 3 carbon atoms, or alkoxy of from one to 3 carbon atoms, with the proviso that not more than two phenyl substitutents are other than alkyl, m is one, 2, 3, 4, or 5, and n is zero, one, 2, 3, or 4; and wherein M$_1$ is $\alpha$-hydroxy:$\beta$-methyl or $\alpha$-hydroxy:$\beta$-hydrogen.

Examples of phenyl esters substituted in the para position (i.e., X$_1$ is —COOR$_1$, R$_1$ is p-substituted phenyl) include
- p-acetamidophenyl ester,
- p-benzamidophenyl ester,
- p-(p-acetamidobenzamido)phenyl ester,
- p-(p-benzamidobenzamido)phenyl ester,
- p-amidocarbonylamidophenyl ester,
- p-acetylphenyl ester,
- p-benzylphenyl ester,
- p-amidocarbonylphenyl ester,
- p-methoxycarbonylphenyl ester,
- p-benzoyloxyphenyl ester,
- p-(p-acetamidobenzoyloxy)phenyl ester and
- p-hydroxybenzaldehyde semicarbazone ester.

Examples of novel amides herein (i.e., X$_1$ is COL$_4$) include the following:

(1) Amides within the scope of alkylamido groups of the formula —NR$_{21}$R$_{22}$ are
- methylamide,
- ethylamide,
- n-propylamide,
- n-butylamide,
- n-pentylamide,
- n-hexylamide,
- n-heptylamide,
- n-octylamide,
- n-nonylamide,
- n-decylamide,
- n-undecylamide, and
- n-dodecylamide, and isomeric forms thereof. Further examples are
- dimethylamide,
- diethylamide,
- di-n-propylamide,
- di-n-butylamide,
- methylethylamide,
- methylpropylamide,
- methylbutylamide,
- ethylpropylamide,
- ethylbutylamide and
- propylbutylamide.

Amides within the scope of cycloalkylamido are
- cyclopropylamide,
- cyclobutylamide,
- cyclopentylamide,
- 2,3-dimethylcyclopentylamide,
- 2,2-dimethylcyclopentylamide,
- 2-methylcyclopentylamide,
- 3-tert-butylcyclopentylamide,
- cyclohexylamide,
- 4-tert-butylcyclohexylamide,
- 3-isopropylcyclohexylamide,
- 2,2-dimethylcyclohexylamide,
- cycloheptylamide,
- cyclooctylamide,
- cyclononylamide,
- cyclodecylamide,
- N-methyl-N-cyclobutylamide,
- N-methyl-N-cyclopentylamide,
- N-methyl-N-cyclohexylamide,
- N-ethyl-N-cyclopentylamide,
- N-ethyl-N-cyclohexylamide,
- dicyclopentylamide, and
- dicyclohexylamide.

Amides within the scope of aralkylamido are
- benzylamide,
- 2-phenylethylamide,
- 2-phenylethylamide,
- N-methyl-N-benzylamide, and
- dibenzylamide.

Amides within the scope of substituted phenylamido and p-chloroanilide,
- m-chloroanilide,
- 2,4-dichloroanilide,
- 2,4,6-trichloroanilide,
- m-nitroanilide,
- p-nitroanilide,
- p-methoxyanilide,
- 3,4-dimethoxyanilide,
- 3,4,5-trimethoxyanilide,
- p-hydroxymethylanilide,
- p-methylanalide,
- m-methylanilide,
- p-ethylanilide,
- t-butylanilide,
- p-carboxyanilide,
- p-methoxycarbonylanilide,
- o-carboxyanilide and
- o-hydroxyanilide.

Amides within the scope of carboxyalkylamido are
- carboxyalkylamido,
- carboxymethylamide,
- carboxyethylamide,
- carboxypropylamide, and
- carboxybutylamide.

Amides within the scope of the carbamoylalkylamido are
- carbamoylmethylamide,
- carbamoylethylamide,
- carbomoylpropylamide, and
- carbamoylbutylamide.

Amides within the scope of cyanoalkylamido are
- cyanomethylamide, cyanoethylamide,
cyanopropylamide and
cyanobutylamide.

Amides within the scope of acetylalkylamido are
acetylmethylamide,
acetylethylamide,
acetylpropylamide, and
acetylbutylamide.

Amides within the scope of benzoylalkylamido are
benzoylmethylamide,
benzoylethylamide,
benzoylpropylamide, and
benzoylbutylamide.

Amides within the scope of substituted benzoylalkylamido are
p-chlorobenzoylmethylamide,
m-chlorobenzoylmethylamide,
2,4-dichlorobenzoylmethylamide,
2,4,6-tri-chlorobenzoylmethylamide,
m-nitrobenzoylmethylamide,
p-nitrobenzoylmethylamide,
p-methoxybenzoylmethylamide,
2,4-dimethoylbenzoylmethylamide,
3,4,5-trimethoxybenzoylmethylamide,
p-hydroxymethylbenzoylmethylamide,
p-methylbenzoylmethylamide,
m-methylbenzoylmethylamide,
p-ethylbenzoylmethylamide,
t-butylbenzoylmethylamide,
p-carboxybenzoylmethylamide,
m-methoxycarbonylbenzoylmethylamide,
o-carboxybenzoylmethylamide,
o-hydroxybenzoylmethylamide,
p-chlorobenzoylethylamide,
m-chlorobenzoylethylamide,
2,4-dichlorobenzoylethylamide,
2,4,6-trichlorobenzoylethylamide,
m-nitrobenzoylethylamide,
p-nitrobenzoylethylamide,
p-methoxybenzoylethylamide,
p-methoxybenzoylethylamide,
2,4-dimethoxybenzoylethylamide,
3,4,5-trimethoxybenzoylethylamide,
p-hydroxymethylbenzoylethylamide,
p-methylbenzoylethylamide,
m-methylbenzoylethylamide,
p-ethylbenzoylethylamide,
t-butylbenzoylethylamide,
p-carboxybenzoylethylamide,
m-methoxycarbonylbenzoylethylamide,
o-carboxybenzoylethylamide,
o-hydroxybenzoylethylamide,
p-chlorobenzoylpropylamide,
m-chlorobenzoylpropylamide,
2,4-dichlorobenzoylpropylamide,
2,4,6-trichlorobenzoylpropylamide,
m-nitrobenzoylpropylamide,
p-nitrobenzoylpropylamide,
p-methoxybenzoylpropylamide,
2,4-dimethoxybenzoylpropylamide,
3,4,5-trimethoxybenzoylpropylamide,
p-hydroxymethylbenzoylpropylamide,
p-methylbenzoylpropylamide,
m-methylbenzoylpropylamide,
p-ethylbenzoylpropylamide,
t-butylbenzoylpropylamide,
p-carboxybenzoylpropylamide,
m-methoxycarbonylbenzoylpropylamide,
o-carboxybenzoylpropylamide,
o-hydroxybenzoylpropylamide,
p-chlorobenzoylbutylamide,
m-chlorobenzoylbutylamide,
2,4-dichlorobenzoylbutylamide,
2,4,6-trichlorobenzoylbutylamide,
m-nitrobenzoylmethylamide,
p-nitrobenzoylbutylamide,
p-methoxybenzoylbutylamide,
2,4-dimethoxybenzoylbutylamide,
3,4,5-trimethoxybenzoylbutylamide,
p-hydroxymethylbenzoylbutylamide,
p-methylbenzoylbutylamide,
m-methylbenzoylbutylamide,
p-ethylbenzoylbutylamide,
t-butylbenzoylbutylamide,
p-carboxybenzoylbutylamide,
m-methoxycarbonylbenzoylbutylamide,
o-carboxybenzoylbutylamide,
o-hydroxybenzoylmethylamide.

Amides within the scope of pyridylamido are
4-methyl-α-pyridylamide,
β-pyridylamide, and
γ-pyridylamide.

Amides within the scope of substituted pyridylamido are
4-methyl-α-pyridylamide,
4-methyl-β-pyridylamide,
4-chloro-α-pyridylamide, and
4-chloro-β-pyridylamide.

Amides within the scope of pyridylalkylamido are
α-pyridylmethylamide,
β-pyridylmethylamide,
γ-pyridylmethylamide,
α-pyridylethylamide,
β-pyridylethylamide,
γ-pyridylethylamide,
α-pyridylpropylamide,
β-pyridylpropylamide,
γ-pyridylpropylamide,
α-pyridylbutylamide,
β-pyridylbutylamide, and
γ-pyridylbutylamide.

Amides within the scope of substituted pyridylalkylamido are
4-methyl-α-pyridylmethylamide,
4-methyl-β-pyridylmethylamide,
4-chloropyridylmethylamide,
4-chloro-β-pyridylmethylamide,
4-methyl-α-pyridylethylamide,
4-methyl-β-pyridylethylamide,
4-chloropyridethylamide,
4-chloro-β-pyridylethylamide,
4-methyl-α-pyridylpropylamide,
4-methyl-β-pyridylpropylamide,
4-chloropyridylpropylamide,
4-chloro-β-pyridylpropylamide,
4-methyl-β-pyridylbutylamide,
4-methyl-α-pyridylbutylamide,
4-chloropyridylbutylamide,
4-chloro-β-pyridylbutylamide,
4-methyl-β-pyridylbutylamide.

Amides within the scope of hydroxyalkyl are
hydroxymethylamide,
α-hydroxyethylamide,
β-hydroxyethylamide,
α-hydroxypropylamide,
β-hydroxypropylamide, γ-hydroxypropylamide,
1-(hydroxymethyl)ethylamide,
1-(hydroxymethyl)propylamide,
(2-hydroxymethyl)propylamide, and
α,α-dimethyl-β-hydroxyethylamide.
Amides within the scope of dihydroxyalkylamide are dihydroxymethylamide,
    α,α-dihydroxyethylamide,
    α,β-dihydroxyethylamide,
    β,β-dihydroxyethylamide,
    α,α-dihydroxypropylamide,
    αβ-dihydroxypropylamide,
    α,γ-dihydroxypropylamide,
    β,β-dihydroxypropylamide,
    β,γ-dihydroxypropylamide,
    γ,γ-dihydroxypropylamide,
    1-(hydroxymethyl)-2-hydroxyethylamide,
    1-(hydroxymethyl)-1-hydroxyethylamide,
    α,α-dihydroxybutylamide,
    α,β-dihydroxybutylamide,
    α,γ-dihydroxybutylamide,
    α,δ-dihydroxybutylamide,
    α,δ-dihydroxybutylamide,
    β,β-dihydroxybutylamide,
    β,γ-dihydroxybutylamide,
    β,δ-dihydroxybutylamide,
    γ,γ-dihydroxybutylamide,
    γ,δ-dihydroxydroxybutylamide,
    δ,δ-dihydroxybutylamide, and
    1,1-bis(hydroxymethyl)ethylamide.
Amides within the scope of trihydroxyalkylamino are
    tris(hydroxymethyl)methylamide and
    1,3-dihydroxy-2-hydroxymethylpropylamide.

(2) Amides within the scope of the cycloamido groups described above are
    pyrrolidylamide,
    piperidylamide,
    morpholinylamide,
    hexamethyleneiminylamide,
    piperazinylamide,
    pyrrolinylamide, and
    3,4-didehydropiperidinylamide.

(3) Amides within the scope of carbonylamido of the formula —$NR_{23}COR_{21}$ are
    methylcarbonylamide,
    ethylcarbonylamide,
    phenylcarbonylamide, and
    benzylcarbonylamide.
Amides within the scope of sulfonylamido of the formula —$NR_{21}SO_2R_{21}$ are
    methylsulfonylamide,
    ethylsulfonylamide,
    phenylsulfonylamide,
    p-tolylsulfonylamide,
    benzylsulfonylamide, (4) Hydrazines within the scope of the above hydrazino groups are
    hydrazine,
    N-aminopiperidine,
    benzoylhydrazine,
    N-aminomorpholine,
    2-hydroxyethylhydrazine,
    methylhydrazine,
    2,2,2-hydroxyethylhydrazine and
    p-carboxyphenylhydrazine.

Examples of alkyl of one to 12 carbon atoms, inclusive, are
    methyl,
    ethyl,
    propyl,
    butyl,
    pentyl,
    hexyl,
    heptyl,
    octyl,
    nonyl,
    decyl,
    undecyl,
    dodecyl, and
isomeric forms thereof.

Examples of cycloalkyl of 3 to 10 carbon atoms, inclusive, which includes alkyl-substituted cycloalkyl, are
    cyclopropyl,
    2-methylcyclopropyl,
    2,2-dimethylcyclopropyl,
    2,3-diethylcyclopropyl,
    2-butylcyclopropyl,
    cyclobutyl,
    2-methylcyclobutyl,
    3-propylcyclobutyl,
    2,3,4-triethylcyclobutyl,
    cyclopentyl,
    2,2-dimethylcyclopentyl,
    2-pentylcyclopentyl,
    3-tert-butylcyclopentyl,
    cyclohexyl,
    4-tert-butylcyclohexyl,
    3-isopropylcyclohexyl,
    2,2-dimethylcyclohexyl,
    cycloheptyl,
    cyclooctyl,
    cyclononyl and
    cyclodecyl.

Examples of aralkyl of 7 to 12 carbon atoms, inclusive, are benzyl,
    2-phenethyl,
    1-phenylethyl,
    2-phenylpropyl,
    4-phenylbutyl,
    3-phenylbutyl,
    2-(1-naphthylethyl), and
    1-(2-naphthymethl).

Examples of phenyl substituted by one to 3 chloro or alkyl of one to 4 carbon atoms, inclusive, are
    p-chlorophenyl,
    m-chlorophenyl,
    2,4-dichlorophenyl,
    2,4,6-trichlorophenyl,
    p-tolyl,
    m-tolyl,
    o-tolyl,
    p-ethylphenyl,
    p-tert-butylphenyl,
    2,5-dimethylphenyl,
    4-chloro-2-methylphenyl, and
    2,4-dichloro-3-methylphenyl.

Examples of —(PhI) are
    phenyl,
    (o-, m-, or p-)tolyl,
    (o-, m-, or p-)ethylphenyl,
    2-ethyl-tolyl,
    4-ethyl-o-tolyl,
    5-ethyl-m-tolyl,
    (o-, m-, or p-)propylphenyl,
    2-propyl-(o-, m-, or p-)tolyl,
    4-isopropyl-2,6-xylyl, 3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-,4-,5- or 6-)chloro-o-tolyl,
4-chloro-2-propylphenyl,
2-isopropyl-4-chlorophenyl,
4-chloro-3,5-xylyl,
(2,3- 2,4- 2,5- 2,6- or 3,5-)dichlorophenyl,
4-chloro-3-fluorophenyl,
(3- or 4-)chloro-2-fluorophenyl,
o-, m-, or p-)trifluoromethylphenyl,
(o-, m-, or p-)ethoxyphenyl,
(4- or 5-)chloro-2-methoxyphenyl, and
2,4-dichloro-(5- or 6-)methylphenyl.

With regard to the divalent substituents described above (e.g. $L_1$ and $M_1$), these divalent radicals are defined as $\alpha$-$R_1$:$\beta$-$R_j$, wherein $R_i$ represents the substituent of the divalent moiety in the alpha configuration with respect to the ring and $R_j$ represents the substituent of the divalent moiety in the beta configuration with respect to the plane of the ring. Accordingly, when $M_1$ is defined as $\alpha 13$ OH:$\beta$—H, the hydroxy of the $M_1$ moiety is in the alpha configuration, and the hydrogen substituent is in the beta configuration. The wavy line at $R_{67}$ represents substituents in the alpha or beta configuration.

While the compounds of the present invention are derivatives of prostaglandin analogs, they will be named herein as analogs of long chain fatty acids, using the Chemical Abstracts numbering system (see Naming and Indexing of Chemical Substances for Chemical Abstracts during the Ninth Collective Period (1972-1976), a reprint of section IV from the Volume 76 Index Guide.) A heptadecadienoic acid will be formed whenever a prostaglandin analog of 20 carbon chain length is used as the starting material.

The novel compounds of this invention are highly active as inhibitors of the thromboxane synthetase enzyme system. Accordingly, these novel compounds are useful for administration to mammals, including humans, whenever it is desirable medically to inhibit this enzyme system. For example, these novel compounds are useful as antiinflammatory agents in mammals and especially humans, and for this purpose, are administered systemically and preferably orally. For oral administration, a dose range of 0.5 to 50 mg per kg of human body weight is used to give relief from pain associated with inflammatory disorders such as rheumatoid arthritis. They are also administered intraveneously in aggravated cases of inflammation, preferably in a dose range 0.01 to 100 $\mu$g per kg per minute until relief from pain is attained. When used for these purposes, these novel compounds cause fewer and lesser undesirable side effects than do the known sythetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These prostaglandins are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intraveneously, subcutaneously, intramusculary, and in the form of sterile implants for prolonged action. For rapid response especially in emergency situations, the intraveneous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation of perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the preferred body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

When $X_1$ is —COOR$_1$, the novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel compounds of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
 1-methylpiperidine,
 4-ethylmorpholine,
 1-isopropylpyrrolidine,
 2-methylpyrrolidine,
 1,4-dimethylpiperazine,
 2-methylpiperidine,
and the like, as well as amines containing water-solubilizing or hydrophilic groups, e.g,
 mono-, di-, and triethanolamine,
 ethyldiethanolamine,
 N-butylethanolamine,
 2-amino-1-butanol,
 2-amino-2-ethyl-1,3-propanediol,
 2-amino-2-methyl-1-propanol,
 tris(hydroxymethyl)aminomethane,
 N-phenylethanolamine,
 N-(p-tert-amylphenyl)diethanolamine,
 glactamine,
 N-methylglycamine,
 N-methylglucosamine,
 ephedrine,
 phenylephrine,
 epinephrine,
 procaine,
and the like. Further useful amine salts are the basic amino acid salts, e.g.,
 lysine and
 arginine.

Examples of suitable pharmacologically acceptable quaternary ammonium cations are
 tetramethylammonium,
 tetraethylammonium,
 benzyltrimethylammonium,
 phenyltriethylammonium, and the like.

Certain compounds of the present invention are preferred to obtain the optimal combination of biological response, specificity, potency, and duration of activity. Thus, compounds of the formula II are preferred, and compounds wherein $X_1$ is $CO_2H$ or $CO_2CH_3$, $Z_1$ is $CH-CH-CH_2CH_2CH_2-$, $R_3$ and $R_4$ are hydrogen, $R_7$ is $-(CH_2)_3CH_3$, or $P_1$ is $-C(OH)(H)CH_2-C(H)=CH_2$ are also preferred. Compounds which satisfy one or more of these preferences are preferred and compounds satisfying all of these preferences are most preferred.

Compounds of the present invention are prepared by the method depicted in Chart A-C.

In the Charts, $-Si(G_1)_3$ is a silyl protective group, OTCEC is trichloroethylcarbonate and $M_2$ is α-H:β-O-Si($G_1$)$_3$ or β-H:α-O-Si($G_1$)$_3$, $M_3$ is α-H:β-OTCEC or β-H:α-OTCEC, and ACO is an acetoxy group.

In the formula -Si($G_1$)$_3$, $G_1$ is alkyl of one to 4 carbon atoms. cycloalkyl of 3 to 10 carbon atoms, inclusive, aralkyl of 7 to 12 carbon atoms, inclusive, phenyl, or phenyl substituted with one or 2 fluoro, chloro or alkyl of one to 4 carbon atoms, with the proviso that in each $-Si(G_1)_3$ moiety the various $G_1$'s are the same or different. Silyl groups within the scope of $-Si(G_1)_3$ include dimethylphenylsilyl, triphenylsilyl, t-butyldimethylsilyl, or methylphenylbenzylsilyl. With regard to $G_1$, examples of alkyl are
 methyl,
 ethyl,
 propyl,
 isobutyl,
 butyl,
 sec-butyl,
 tert-butyl,
 pentyl,
and the like. Examples of aralkyl are
 benzoyl,
 phenethyl,
 α-phenylethyl,
 3-phenylpropyl,
 α-naphthylmethyl,
 and 2-(α-naphthyl)ethyl.
Examples of phenyl substituted with halo or alkyl are
 p-chlorophenyl,
 m-fluorophenyl,
 o-tolyl,
 2,4-dichlorophenyl,
 p-tert-butylphenyl,
 4-chloro-2-methylphenyl, and
 2,4-dichloro-3-methylphenyl.

Terbutyldimethylsilyl is most preferred as a silylating agent. These silyl groups are known in the art. See for example, Pierce "Silylation of Organic Compounds," Pierce Chemical Company, Rockford, Ill. (1968).

The preparation of the compounds of the present invention is first begun by selectively silylating a PGF-type prostaglandin, as depicted in Chart A. (PGF-type prostaglandins are well known and readily available compounds see, e.g., U.S. Pat. Nos. 3,069,322; 3,852,337; 3,776,939; 3,796,740; 3,796,741; 3,804,880; 3,796,743; 3,706,789; 3,852,316; 3,953,499; 3,855,270; 3,726,909; 3,816,508; 3,936,487; 3,923,861; 3,920,724; 3,923,865; 3,944,595; 3,928,448; 3,933,896; 3,983,154; 3,974,200; 3,87,083; 4,00,263; 3,987,087; 3,996,267; 3,983,157; 3,804,890; 3,954,833; 3,904,679; and 3,845,115.)

Thus, 2 equivalents of a PGF-type compound of the formula X are treated with trichloroethyl chloroformate in dry pyridine at −50° for 5 hr. Workup provides the 11,15-bis-(trichloroethyl carbonate) of the formula XI. This compound is then dissolved in dimethylformamide (DMF) and treated with 1.5 equivalents of tert-butyldimethylsilylchloride and 1.5 equivalents of imidazole at 25° under nitrogen. After 4 hr the mixture is worked up to yield the t-butyldimethylsiloxy-bis-trichloroethylcarbonato-PGF type compound of the formula XII. This compound is then treated with an excess of elemental zinc/ammonium chloride in methanol at 0° for 4 hr., to give the t-butyldimethyl silyl ether of the formula XIII. This is then treated with 1.0 equivalents of tert-butyldimethylsilyl chloride and 1.0 equivalent of imidazole in DMF at −20° for 2 days to give, following chromatographic separation of the regioisomers, the t-butyldimethylsiloxy-PGF derivative of the formula XX.

The compounds of the present invention are prepared from the formula XX compounds by the methods depicted in charts B and C. In Chart B compound XX is treated with excess lead tetra-acetate in benzene or toluene to give a pair of acetoxy-aldehydes, represented by formulas XXI and XXII. This reaction is known in the art, (see, e.g., Schneider and Morge, Tet. Let. 37:3823 (1976)). These compounds are not separated or isolated but are immediately dissolved in dry tetrahydrofuran at −78° C. and treated with the anion of methylphenyl-N-methylsulfoximine. The product of this reaction is then treated with aluminum amalgam in acetic acid, to yield a pair of compounds of structure XXIII and XXIV. Removal of the acetate and methyl ester from XXIII by alkaline hydrolysis, followed by removal of the silyl groups with tetra-n-butyl ammonium fluoride in THF, gives compounds of the present invention in which $P_1$ is C(H)(OH)—CH$_2$—C(H)=CH$_2$.

In Chart C, compounds of the present invention are prepared wherein $P_1$ is C(H)(OH)—CH$_2$—C≡N. As in chart B a compound of formula XX is dissolved in benzene or toluene and treated with lead tetraacetate. After 4 hr, more lead tetraacetate is added and a stream of ammonia is passed through the reaction, (see, e.g., K. N. Parameswaran and O. M. Friedman, Chem. Ind. 988 (1965)) to give the nitriles of formulas XXV and XXVI. Removal of protecting groups as before gives the compounds of the invention.

To prepare compounds of the present invention wherein $P_1$ is —C(H)(OH)—C(=CH$_2$)—(O)H; the compounds of formula XXI and XXII (chart B) are reacted with a Mannich salt (e.g., of the formula $H_2C=N^{\oplus}(CH_3)_2I^{(-)}$). Treatment with methyliodide results in $\beta$ elimination, and the compounds of the invention are then produced by the normal sequence of protecting group hydrolysis.

To prepare compounds of the present invention in which $P_1$ is C(H)(OH)—C(=CH$_2$)—C≡N, the procedure of the preceding paragraph is followed, and the resultant compounds are first treated with lead tetraacetate and ammonia in benzene (as for compounds XV and XVI) and then with sodium bicarbonate in methanol, followed by tetra-n-butylammonium fluoride in THF to give the compound of the invention.

For compounds wherein $R_{67}$ is halogen, the compounds which are recovered from the alkaline hydrolysis (e.g. alcohols) are then treated with tri-n-octyl phosphine in bromoform to give the corresponding bromides, or in chloroform to give the corresponding chlorides, etc. Removal of the silyl ethers with fluoride then gives the compounds of the invention.

Esters of the compounds of the present invention are prepared directly from the esters represented in formula XX. Alternatively, they may be prepared from the parent acids by means well known in the art, (e.g., by treatment of the parent acids with the corresponding alkyl or aryl or phenyl-phenacyl iodides or bromides in the presence of diisopropylethylamine).

DESCRIPTION OF THE PREFERRED EMBODIMENTS

The operation of the present invention is more fully understood by the examples given below:

Preparation 1:

15-(t-butyldimethylsilyl ether) PGF$_2\alpha$, methyl ester, 9-(diphenyl t-butylsilyl ether).

Refer to Chart B.

A 200 ml round bottomed flask equipped with nitrogen inlet and magnetic stirrer is charged with 5.0 g (8.25 mmols) of 9-(diphenyl t-butylsilyl ether)-PGF$_2\alpha$, methyl ester dissolved in 100 ml dry dimethylformamide and the solution is cooled to −50° with acetonitrile/dry ice. The solution is treated with 730 mg of imidazole (1.05 equiv) followed by 1.616 g of t-butyldimethylsilyl chloride (1.05 eq) and the mixture is stirred at −50° under nitrogen until homogeneous (30 min). The vessel is then stoppered, transferred to a freezer at −20°, left 36 hr, quenched by the addition of 50 ml of 2 M potassium bisulfate and washed in a separatory funnel with ethyl acetate. The mixture is then washed with brine, the organic layer is dried over sodium sulfate, the solvent is evaporated, and the resultant crude oil is chromatographed in 500 g of silica packed and eluted with 10% ethyl acetate/hexane in 20 ml fractions. Fractions 41–51 contain 2.85 g (48%) of the desired product.

TLC (silica gel GF: Rf=0.54 in 20% ethyl acetate/hexane (least polar of the two compounds).

The IR spectrum exhibits peaks at 3500, 2950, 1740, 1420, 1250, 1100, 970, 835, 775, 740, and 705 cm$^{-1}$.

The NMR spectrum (CDCl$_3$, TMS) exhibits peaks at $\delta$ 0.94 (s); 1.04 (s); 1.1–2.4 (m); 3.60 (s, 3H); 3.7–4.2 (m, 3H); and 5.2–5.5 (m, 4H).

The mass spectrum (TMS derivative) reveals the following:

Calculated for $C_{42}H_{67}Si_3O_5$: 735.4296 Found: 735.4264.

Major ions: m/e 663, 647, 603, 446, 315, 271, 215, 199.

Preparation 2:

[4R, 7E, 6ξ,15S]-7-[4,6,9-trihydroxy-1,7-tetradecadiene-4-yl, 4-(diphenyl-t-butylsilyl ether), 6-acetoxy, 9-(t-butyldimethylsilyl ether)]-5-Heptenoic acid, methyl ester and

[4R,6E,8ξ,9S]-7[4,8,9-trihydroxy-1,6-tetradocadione-4-yl, 4(diphenyl t-butylsilyl ether), 8-acetoxy, 9-(t-butyldimethylsilyl ether)]-5-Heptenoic acid, methyl ester.

A 250 ml round-bottomed flask is flame dried under nitrogen and charged with 2.3 g (3.2 mmoles) of the alcohol of Preparation 1. The material is dissolved in 100 ml dry toluene and stirred under nitrogen at 65° in an oil bath. A 2.3 g aliquot of crystalline lead tetracetate is added at once and the mixture stirred at 65°–70° for 50 min. At this time 0.75 ml of ethylene glycol is added, the mixture is allowed to stir for a few minutes more, and then transferred to a separatory funnel containing ethyl acetate. The organic layer is washed with brine, and the dried (sodium sulfate) solvent is evaporated to give the crude aldehyde as a yellow oil.

A second 250 ml round-bottomed flask is flame dried and equipped with an addition funnel, nitrogen inlet, septum, and magnetic stirrer. A 1.3 g sample of N-methyl-(S-phenyl, S-methyl) sulfoximine (2.55 equivalents) is weighed out in a flame dried pipette and added to the reaction vessel. 100 ml of tetrahydrofuran is added and the stirred solution is cooled to 0°. To this solution is added 2.55 ml of 2.95 M methyl magnesium chloride (2.50 equiv) using an oven dried syringe, via the septum. The solution is stirred for 30 min at 0°, then cooled to −80°. The crude aldehyde from the previous reaction is dissolved in 20 ml dry tetrahydrofuran and added dropwise to the solution of the sulfoximine anion via the addition funnel over a period of 10 min. After 15 min the reaction is complete, and 50 ml of 2 M potassium bisulfate is added at once and the cooling bath is removed. The icy slurry is decanted into a separatory funnel, washed with brine and extracted with ethyl acetate, and the dried (sodium sulfate) solution is evaporated to give a light yellow oil.

This material is then dissolved in 20 ml of tetrahydrofuran, 10 ml of acetic acid, and 10 ml of water. A batch of aluminum amalgam is prepared in the usual manner and is added immediately to the mechanically stirred solution of the sulfoximine adduct in a 250 ml r.b. flask equipped with a nitrogen inlet and a neutral water (ambient temperature) bath. The reduction is complete in 30 min, at which time the reaction slurry is filtered through celite, the filtrate taken up in ethyl acetate and washed well with saturated sodium bicarbonate (to remove thiophenyl), with potassium bisulfate, and further with brine, and the solution is then dried over sodium sulfate and the solvent is evaporated. The crude oil thus obtained is immediately chromatographed over 700 g of silica gel packed and eluted with 10% ethyl acetate/hexane in 20 ml fractions. Fractions obtained contain both titled compounds. They are recombined and rechromatographed on 85 g of HPLC grade silica gel packed and eluted with 10% ether/hexane, and collected in 10 ml fractions. 5-heptenoic acid, 7[4,8,9-trihydroxy-1,6-tetradocadione-4-yl, 4(diphenyl t-butylsilyl ether), 8-acetoxy, 9(t-butyldimethylsilyl ether)-, [4R,6E,8ξ,9S] eluted first, and 330 mg are obtained from the early fractions, as a mixture of approximately 5% 14-α-acetoxy in the major, 14-β-acetoxy compound. 5-Heptenoic acid, 7-[4,6,9-trihydroxy-1,7-tetradecadiene-4-yl, 4-(diphenyl-t-butylsilyl ether), 6-acetoxy, 9-(t-butyldimethylsilyl)]-[4R,7E,6ξ,15S]methyl ester is epimerically pure and is more polar, eluting in later fractions, from which 381 mg are recovered. The yield is 33% based on the starting alcohol.

TLC analysis (silica gel GF) yields the following: 5-Heptenoic acid, 7-[4,6,9-trihydroxy-1,7-tetradecadiene-4-yl, 4-(diphenyl-t-butylsilyl ether), 6-acetoxy, 9-(t-butyldimethylsilyl ether)]-[4R,7E,6ξ,15S]methyl ester—Rf=0.23 in 10% ethyl acetate/hexane. 5-Heptenoic acid, 7[4,8,9-trihydroxy-1,6-tetradocadione-4-yl, 4(diphenyl t-butylsilyl ether), 8-acetoxy, 9(t-butyldimethylsilyl ether)-, [4R,6E,8ξ,9S]—Rf=0.27 in 10% ethyl acetate/hexane.

The NMR Spectrum (CDCl$_3$, TMS) exhibits peaks as follows: 5-Heptenoic acid, 7-[4,6,9-trihydroxy-1,7-tetradecadiene-4-yl, 4-(diphenyl-t-butylsilyl ether), 6-acetoxy, 9-(t-butyldimethylsilyl ether)]-[4R,7E,6ξ,15S]-methyl ester—δ 0.9 (s); 1.08 (s); 1.1–2.4 (m); 3.67 (s, 3H); 3.8–4.05 (m, 2H); 4.8–5.6 (m); and 7.3–7.7 (m). 5-Heptenoic acid, 7[4,8,9-trihydroxy-1,6-tetradocadione-4-yl, 4(diphenyl t-butylsilyl ether), 8-acetoxy, 9(t-butyldimethylsilyl ether)-, [4R,6E,8ξ,9S]—δ 0.9 (s); 1.08 (s); 1.1–2.4 (m); 3.6–3.7 (sharp singlet, 3H, mashed into a fuzzy multiplet, 1H); 4.6–5.4 (m); and 7.3–7.7 (m).

C$^{13}$ NMR spectrum (CDCL$_3$, TMS) exhibits peaks as follows: 5-Heptenoic acid, 7-[4,6,9-trihydroxy-1,7-tetradecadiene-4-yl, 4-(diphenyl-t-butylsilyl ether), 6-acetoxy, 9-(t-butyldimethylsilyl ether)]-[4R,7E,6ξ,15S]-methyl ester—176.96, 172.89, 139.61, 138.98, 133.19, 133.05, 131.05, 130.93, 129.98, 120.41, 77.05, 76.88, 76.47, 54.88, 50.54, 42.46, 41.68, 37.05, 35.29, 30.67, 30.32, 29.40, 28.27, 27.73, 26.09, 24.62, 22.92, 17.52 (ppm). 5-Heptenoic acid, 7[4,8,9-trihydroxy-1,6-tetradocadione-4-yl, 4(diphenyl t-butylsilyl ether), 8-acetoxy, 9(t-butyldimethylsilyl ether)-, [4R,6E,8ξ,9S]—177.05, 173.02, 139.96, 139.27, 138.56, 138.03, 137.78, 137.50, 137.37, 137.10, 133.60, 132.91, 132.76, 132.42, 131.51, 131.35, 130.82, 130.66, 130.34, 120.17, 81.89, 80.40, 79.07, 78.69, 78.54, 76.20, 54.61, 50.55, 42.80, 36.79, 36.17, 35.34, 32.56, 30.33, 30.10, 29.76, 29.62, 29.08, 28.06, 27.75, 25.81, 24.54, 22.78, 21.31, 17.25 (ppm). Note: Underlined numbers refer to minor peaks due to approx. 10% trans Δ5 isomer.

EXAMPLE 1

[5Z,8R(S),9E,11ξ,12S]-11,12-dihydroxy-8-(1-hydroxy-3-butenyl)-5,9-heptadecadienoic acid (formula III, wherein P$_1$ is —C(OH)(H)—CH$_2$—C(H)=CH$_2$, R$_{67}$ is β-hydroxy; M$_1$ is α-OH:β-H; R$_3$ and R$_4$ are hydrogen, Z$_1$ is cis-CH=CH—CH$_2$—CH$_2$—CH$_2$—, X$_1$ is —COOH, and R$_7$ is —CH$_2$—CH$_2$—CH$_2$—CH$_3$) and [5Z,8R(S),9E,11ξ,12S]-11,12-dihydroxy-8-(1-hydroxy-3-butenyl)-5,9-heptadecadienoic acid (formula III wherein P$_1$ is —C(OH)(H)—CH$_2$—C(H)=CH$_2$, R$_{67}$ is α-hydroxy; M$_1$ is α-OH:β-H; R$_3$ and R$_4$ are hydrogen, Z$_1$ is cis-CH=CH—CH$_2$—CH$_2$—, X$_1$ is —COOH, and R$_7$ is —CH$_2$—CH$_2$—CH$_2$—CH$_3$).

Refer to Chart B.

A 100 mg sample of [4R,6E,8ξ,9S]-7[4,8,9-trihydroxy-1,6-tetradecadione-4-yl, 4(diphenyl t-butylsilyl ether), 8-acetoxy, 9(t-butyldimethylsilyl ether)-, 5-heptenoic acid, methyl ester is dissolved in 10 m of pure 0.75 M tetra-n-butyl ammonium fluoride solution in tetrahydrofuran and stirred at 25°–40° over 24 hr. The mixture is then taken up in ethyl acetate, washed with water and with brine, and dried over sodium sulfate. The solvent is then evaporated to give an oil. This oil is dissolved in 5 ml of methanol and stirred for 24 hr under nitrogen in the presence of 1 ml of 3 M potassium hydroxide. The reaction is then quenched with acid (2 M potassium bisulfate), and extracted with ethyl acetate. The extracts are washed with brine, and the dried (sodium sulfate) solvents are evaporated to give a crude oil. This oil is then chromatographed on 20 g of CC-4 silica gel packed and eluted with 15% acetone/methylene chloride. The 8-compound is the least polar, eluting first, and 15 mg are recovered. The 8-compound is more polar, 110 mg of pure compound is recovered from the later fractions. The yield is 70% from the fully protected compound.

The NMR spectrum (CDCl$_3$, TMS) exhibits peaks for both isomers at w 0.5–2.5 (m, major peaks at 0.9, 1.35, 2.25; 3.6 (m, 2H); 4.1 (m, 1H); 4.6 (variable, s, 4H, moves upfield on ↓ in []); 5.0–6.05 (m, 7H, 4 major peaks at 5.0, 5.25, 5.4, 5.60).

The IR spectrum exhibits peaks at 3500-2500, λmax at 3.3 and 3.6 microns; 1700, 1400, 1000-950 cm$^{-1}$.

The mass spectrum (TMS derivative) is as follows: weak M$^+$-CH$_3$. Found: 641.3932. Calculated: 641.3909 (nearly identical for both isomers).

The C$^{13}$ NMR spectrum (CDCl$_3$, TMS) exhibits peaks as follows; the only differences in the C$^{13}$ nmr spectra of the two isomers occur in the vinyl and carbinol regions; only these shifts are reported.

[5Z,8R(S),9E,11ξ,12S]-11,12-dihydroxy-8-(1-hydroxy-3-butenyl)-5,9-heptadeca-dienoic acid—134.98, 133.23, 130.54, 130.12, 128.85, 111.71, 75.68, 74.33, and 72.32 ppm.

[5Z,8R(S),9E,11ξ,12S]-11,12-dihydroxy-8-(1-hydroxy-3-butenyl)-5,9-heptadecadienoic acid 134.89, 133.07, 132.75, 129.92, 128.62, 117.69, 75.80, 74.69, and 72.71 ppm.

EXAMPLE 2

[5Z,8S(S),9ξ,10E,12S]-9,12-dihydroxy-8-(1-hydroxy-3-butenyl)-5,10-heptadecadienoic acid (formula II wherein $P_1$ is —C(OH)(H)—$CH_2$—C(H)═$CH_2$, $R_{67}$ is β-hydroxy; $M_1$ is α-OH:β-H; $R_3$ and $R_4$ are hydrogen, $Z_1$ is cis-CH═CH—$CH_2$—$CH_2$—$CH_2$—, $X_1$ is —COOH, and $R_7$ is —$CH_2$—$CH_2$—$CH_2$—$CH_3$).

Refer to Chart B.

A 540 mg sample of 5-Heptenoic acid, 7-[4,6,9-trihydroxy-1,7-tetradecadiene-4-yl, 4-(diphenyl-t-butylsilyl ether), 6-acetoxy, 9-(t-butyldimethylsilyl ether)]-[4R,7E,6ξ,15S]methyl ester is dissolved in 25 ml of 0.75 m tetra-n-butyl ammonium fluoride in tetrahydrofuran and stirred for 6 hr at 25°, and for 20 hr at 45°. It is treated with 10 ml 2 M potassium bisulfate, poured into a separatory funnel and extracted with ethyl acetate. The organic layer is washed with water, and then with brine, and the dried (sodium sulfate) solvents are evaporated to give a crude oil. This is then dissolved in 5 ml of methanol and allowed to stir 3 hr at 25° in the presence of 3 ml of 3 M potassium hydroxide. The mixture is then acidified with 2 M potassium bisulfate, and extracted with ethyl acetate. The extracts are washed with brine, dried over sodium sulfate and the solvent is evaporated. The brown oil thus obtained is chromatographed on 50 g of CC4 silica gel packed and eluted with 20% acetone/methylene chloride. Fractions 80–160 contain 64 mg (25%) of the titled product as a colorless oil.

The TLC (silica gel GF) reveals the following: Rf=0.56 in A-IX system.

The NMR spectrum ($CDCl_3$, TMS) exhibits peaks at: δ 0.9–2.5 (m, major peaks at 0.9, 1.3, 2.2, 2.3, 2.35); 3.70 (m, 1H); 4.2–4.4 (m, 2H); 4.5 (variable, S, 4H); 5.0–6.0 (m, 7H, major peaks at 5.0, 5.3, 5.4, 5.70).

The IR spectrum exhibits peaks at: 3500-2500, λmax at 3.3 and 3.6 microns; 1700, 1400, 100–950, 905 $cm^{-1}$.

The mass spectrum (TMS derivative) reveals the following: Found for $M^+$—$CH_3$: 641.3906. Calculated for $C_{32}H_{65}Si_4O_5$: 641.3903.

The $C^{13}$ NMR spectrum ($CDCl_3$, TMS) exhibits peaks at: 135.06, 134.41, 132.69, 130.46, 128.48, 118.01, 74.11, 72.97, 72.45, 48.12, 40.48, 37.05, 33.18, 31.76, 26.50, 26.31, 25.16, 24.48, 22.61, 14.02 ppm downfield of TMS. The shift underlined is a small (16 units) impurity peak or mechanical glitch.

EXAMPLE 3

Using the procedure of the preceding examples, all of the remaining compounds within the scope of this invention are prepared. Representative examples are compounds prepared from prostaglandins exhibiting the following side chain variations:

- 15-methyl-;
- 16-methyl-;
- 16,16-Dimethyl-;
- 16-Fluoro-;
- 16,16-Difluoro-;
- 17-Phenyl-18,19,20-trinor-;
- 17-(m-trifluoromethylphenyl)-18,19,20-trinor-;
- 17-(m-chlorophenyl)-18,19,20-trinor-;
- 17-(p-fluorophenyl)-18,19,20-trinor-;
- 16-Methyl-17-phenyl-18,19,20-trinor-;
- 16,16-Dimethyl-17-phenyl-18,19,20-trinor-;
- 16-Fluoro-17-phenyl-18,19,20-trinor-;
- 16,16-Difluoro-17-phenyl-18,19,20-trinor-;
- 16-Phenoxy-17,18,19,20-tetranor-;
- 16-(m-trifluoromethylphenoxy)-17,18,19,20-tetranor-;
- 16-(m-chlorophenoxy)-17,18,19,20-tetranor-;
- 16-(p-fluorophenoxy)-17,18,19,20-tetranor-;
- 16-Phenoxy-18,19,20-trinor-;
- 16-Methyl-16-phenoxy-18,19,20-trinor-;
- 13,14-Didehydro-;
- 16-Methyl-13,14-didehydro-;
- 16,16-Dimethyl-13,14-didehydro-;
- 16-Fluoro-13,14-didehydro-;
- 16,16-Difluoro-13,14-didehydro-;
- 17-Phenyl-18,19,20-trinor-13,14-didehydro-;
- 17-(m-trifluoromethylphenyl)-18,19,20-trinor-13,14-didehydro-;
- 17-(m-chlorophenyl)-18,19,20-trinor-13,14-didehydro-;
- 17-(p-fluorophenyl)-18,19,20-trinor-13,14-didehydro-;
- 16-Methyl-17-phenyl-18,19,20-trinor-13,14-didehydro-;
- 16,16-Dimethyl-17-phenyl-18,19,20-trinor-13,14-didehydro-;
- 16-Fluoro-17-phenyl-18,19,20-trinor-13,14-didehydro-;
- 16,16-Difluoro-17-phenyl-18,19,20-trinor-13,14-didehydro-;
- 16-Phenoxy-17,18,19,20-tetranor-13,14-didehydro-;
- 16-(m-trifluoromethylphenoxy)-17,18,19,20-tetranor-13,14-didehydro-;
- 16-(m-chlorophenoxy)-17,18,19,20-tetranor-13,14-didehydro-;
- 16-Phenoxy-18,19,20-trinor-13,14-didehydro-;
- 16-Methyl-16-phenoxy-18,19,20-trinor-13,14-didehydro-;
- 13,14-Dihydro-;
- 16-Methyl-13,14-dihydro-;
- 16,16-Dimethyl-13,14-dihydro-;
- 16-Fluoro-13,14-dihydro-;
- 16,16-Difluoro-13,14-dihydro-;
- 17-Phenyl-18,19,20-trinor-13,14-dihydro-;
- 17-(m-trifluoromethylphenyl)-18,19,20-trinor-13,14-dihydro-;
- 17-(m-chlorophenyl)-18,19,20-trinor-13,14-dihydro-;
- 17-(p-fluorophenyl)-18,19,20-trinor-13,14-dihydro-;
- 16-Methyl-17-phenyl-18,19,20-trinor-13,14-dihydro-;
- 16,16-Dimethyl-17-phenyl-18,19,20-trinor-13,14-dihydro-;
- 16-Fluoro-17-phenyl-18,19,20-trinor-13,14-dihydro-;
- 16,16-Difluoro-17-phenyl-18,19,20-trinor-13,14-dihydro-;
- 16-Phenoxy-17,18,19,20-tetranor-13,14-dihydro-;
- 16-(m-trifluoromethylphenoxy)-17,18,19,20-tetranor-13,14-dihydro-;
- 16-(m-chlorophenoxy)-17,18,19,20-tetranor-13,14-dihydro-;
- 16-(p-fluorophenoxy)-17,18,19,20-tetranor-13,14-dihydro-;
- 16-Phenoxy-18,19,20-trinor-13,14-dihydro-; and
- 16-Methyl-16-phenoxy-18,19,20-trinor-13,14-dihydro-.

FORMULAS
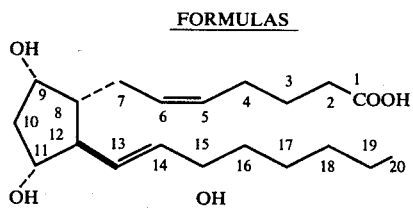
I
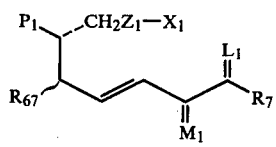
II
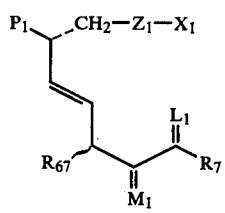
III
CHART A
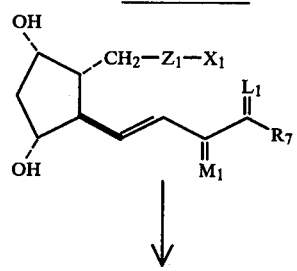
I
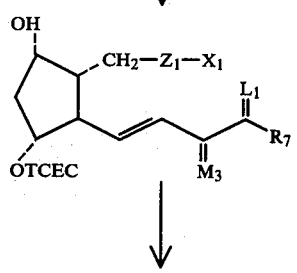
XI
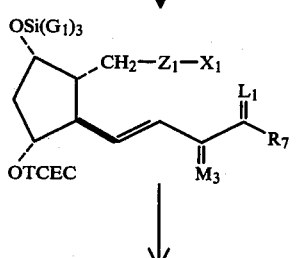
XII
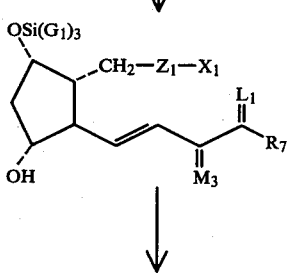
XIII
-continued
CHART A
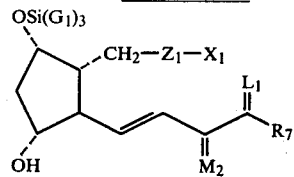
XX
CHART B
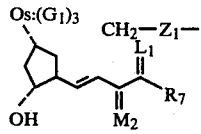
XX
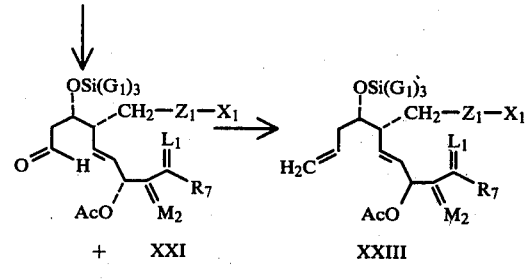
XXI + XXIII
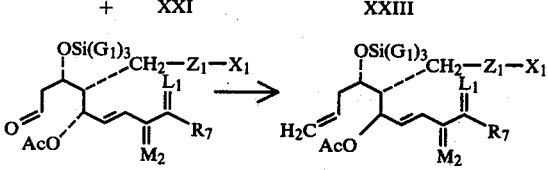
XXII    XXIV
CHART C
XX
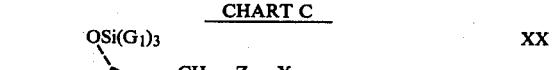
XXV
+
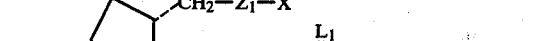
XXVI
I claim:
1. A compound of the formula II or III,

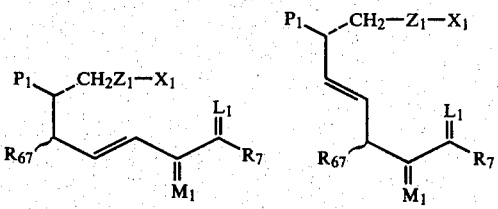

II  III wherein $P_1$ is
(a) $-C(OH)(H)-CH_2-C(H)=CH_2$;
(b) $-C(OH)(H)-CH_2-C\equiv N$;
(c) $-C(OH)(H)-C(=CH_2)C(O)H$; or
(d) $-C(OH)H-C(=CH_2)C\equiv N$;
wherein $R_{67}$ is hydroxy, chloro, bromo, or fluoro;
wherein $X_1$ is
(a) $-CO_2R_1$, wherein $R_1$ is hydrogen, alkyl of from one to 12 carbon atoms, cycloalkyl of 3 to 10 carbon atoms, aralkyl of from 7 to 12 carbon atoms, phenyl, phenyl substituted by one, 2 or 3 chloro or one, 2 or 3 alkyl, or phenyl substituted in the para position by
  (i) $NHC(O)R_{25}$
  (ii) $-O-C(O)R_{26}$,
  (iii) $-CO_2R_1$
  (iv) $-O-C(O)-(p-Ph)-R_{27}$, wherein p—Ph is 1,4-phenylene, or
  (v) $-CH=N-NH-C(O)-NH_2$,
wherein $R_{25}$ is methyl, phenyl, acetamidophenyl, benzoylamidophenyl, or $NH_2$; wherein $R_{26}$ is methyl, phenyl, $NH_2$, or methoxy; wherein $R_{27}$ is hydrogen, acetamido, benzoylamido; or $R_1$ can be a pharmacologically acceptable cation;
(b) $-COW_1$, wherein $W_1$ is
  (i) amido of the formula $-NR_{21}R_{22}$, wherein $R_{21}$ and $R_{22}$ are the same or different and are:
    hydrogen;
    alkyl of one to 12 carbon atoms, inclusive;
    cycloalkyl of 3 to 10 carbon atoms, inclusive;
    aralkyl of 7 to 12 carbon atoms, inclusive;
    phenyl;
    phenyl substituted with one, 2, or 3 chloro, alkyl of one to 3 carbon atoms, inclusive, hydroxy, carboxy, alkoxycarbonyl of one to 4 carbon atoms, inclusive, or nitro;
    carboxyalkyl of one to four carbon atoms, inclusive;
    carbamoylalkyl of one to 4 carbon atoms, inclusive;
    cyanoalkyl of one to 4 carbon atoms, inclusive;
    acetylalkyl of one to 4 carbon atoms, inclusive;
    benzoylalkyl of one to 4 carbon atoms, inclusive;
    benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    pyridyl;
    pyridyl substituted by one, 2, or 3 chloro, alkyl of one to 3 carbon atoms, inclusive, or alkoxy of one to 3 carbon atoms, inclusive;
    pyridylalkyl of one to 4 carbon atoms, inclusive; or
    pyridylalkyl substituted by one, 2, or 3 chloro, alkyl of one to 3 carbon atoms, inclusive, hydroxy, alkoxy of one to 3 carbon atoms, inclusive, hydroxyalkyl of one to 4 carbon atoms, inclusive, dihydroxyalkyl of one to 4 carbon atoms inclusive, or trihydroxyalkyl of one to 4 carbon atoms, inclusive;
    with the further proviso that not more than one of $R_{21}$ and $R_{22}$ is other than hydrogen or alkyl;
  (ii) cycloamido selected from the group consisting of
    1-pyrrolidinyl,
    1-piperidinyl,
    4-morpholinyl,
    hexahydro-1H-azepin-1-yl,
    3-pyrrolin-1-yl, or
    3,6-dihydro-1(2H)-pyridinyl, substituted by $R_{21}$ or $R_{22}$ or both or
    1-piperazinyl substituted at the 4 position by $R_{21}$, wherein $R_{21}$ and $R_{22}$ are as defined above;
  (iii) carbonylamido of the formula $-NR_{23}COR_{21}$, wherein $R_{23}$ is hydrogen or alkyl of one to 4 carbon atoms and $R_{21}$ is as defined above;
  (iv) sulfonylamido of the formula $-NR_{23}SO_2R_{21}$, wherein $R_{21}$ and $R_{23}$ are as defined above; or
  (v) hydrazino of the formula $-NR_{23}R_{24}$, wherein $R_{24}$ is amido of the formula $-NR_{21}R_{22}$, as defined above, or cycloamido, as defined above; or
(c) $CH_2OH$;
(d) $CH_2NR_{31}R_{32}$ wherein $R_{31}$ and $R_{32}$ are the same or different and are hydrogen or alkyl of from one to 4 carbon atoms;
wherein $Z_1$ is
(a) cis—$CH=CH-CH_2(CH_2)_g-CH_2-$;
(b) trans—$CH=CH-CH_2(CH_2)_g-CH_2$;
(c) $-CH=CH-CH_2(CH_2)_gCF_2-$;
(d) trans—$CH=CH-CH_2(CH_2)_g-CH_2-$;
(e) cis—$CH_2-CH=CH-(CH_2)_g-CH_2$;
(f) trans—$CH_2-CH=CH-(CH_2)_g-CH_2$;
(g) $-(CH_2)_3-(CH_2)_g-CH_2$;
(h) $-(CH_2)_3-(CH_2)_g-CF_2$;
(i) $-CH_2-O-CH_2-(CH_2)_g-CH_2-$;
(j) phenyl substituted by $-CH_2(CH_2)_g$ or $-O-(CH_2)_g$, wherein g is one, 2, or three;
wherein $L_1$ is $\alpha-R_3:\beta-R_4$ or $\beta-R_3:\alpha-R_4$ or a mixture of the two, wherein $R_3$ and $R_4$ are the same or different and are hydrogen, methyl, or fluoro, with the proviso that when $R_3$ is fluoro $R_4$ is fluoro and when $R_4$ is fluoro $R_3$ is fluoro;
wherein $R_7$ is
(a) $-(CH_2)_m-CH_3$;
(b) $O-(Ph-s)$; or
(c) $-(CH_2)_n(Ph-s)$; wherein (Ph—s) is phenyl or phenyl substituted by zero, one, 2, or 3 chloro, fluoro, trifluoromethyl, alkyl of from one to 3 carbon atoms, or alkoxy of from one to 3 carbon atoms, with the proviso that not more than two phenyl substitutents are other than alkyl, m is one, 2, 3, 4, or 5, and n is zero, one, 2, 3, or 4; and
wherein $M_1$ is $\alpha$-hydroxy:$\beta$-methyl or $\alpha$-hydroxy:$\beta$-hydrogen.

2. A compound of claim 1, wherein the compound is of the formula II.

3. [5Z,8S(S),9$\xi$,10E,12S]-9,12-dihydroxy-8-(1-hydroxy-3-butenyl)-5,10-heptadecadienoic acid, a compound of claim 2, wherein $P_1$ is $-C(OH)(H)-CH_2-C(H)=CH_2$, $R_{67}$ is $\beta$-hydroxy; $M_1$ is $\alpha-OH:\beta-H$; $R_3$ and $R_4$ are hydrogen, $Z_1$ is cis—$CH=CH-CH-$ $_2$—CH$_2$—CH$_2$—, X$_1$ is —COOH, and R$_7$ is —CH$_2$—CH$_2$—CH$_2$—CH$_3$.

4. A compound of claim 1, wherein the compound is of the formula III.

5. [5Z,8R(S),9E,11ξ,12S]-11,12-dihydroxy-8-(1-hydroxy-3-butenyl)-5,9-heptadecadienoic acid, a compound of claim 4, wherein P$_1$ is —C(OH)(H)—CH$_2$—C(H)=CH$_2$, R$_{67}$ is β-hydroxy; M$_1$ is α—OH:β—H; R$_3$ and R$_4$ are hydrogen, Z$_1$ is cis—CH=CH—CH$_2$—CH$_2$—CH$_2$—, X$_1$ is —COOH, and R$_7$ is —CH$_2$—CH$_2$—CH$_2$—CH$_3$.

6. [5Z,8R(S),9E,11ξ,12S]-11,12-dihydroxy-8-(1-hydroxy-3-butenyl)-5,9-heptadecadienoic acid, a compound of claim 4 wherein P$_1$ is —C(OH)(H)—CH$_2$—C(H)=CH$_2$, R$_{67}$ is α-hydroxy; M$_1$ is α—OH:β—H; R$_3$ and R$_4$ are hydrogen, Z$_1$ is cis—CH=CH—CH$_2$—CH$_2$—CH$_2$—, X$_1$ is —COOH, and R$_7$ is —CH$_2$—CH$_2$—CH$_2$—CH$_3$..

7. A compound according to claim 1, wherein X$_1$ is —COOR$_1$.

8. A compound according to claim 2, wherein Z$_1$ is cis—CH=CH—CH$_2$—(CH$_2$)$_g$—CF$_2$—.

9. A compound according to claim 2, wherein Z$_1$ is cis—CH$_2$—CH=CH—(CH$_2$)$_g$—CH$_2$.

10. A compound according to claim 2, wherein Z$_1$ is —(CH$_2$)$_3$—(CH$_2$)$_g$—CH$_2$—.

11. A compound according to claim 2, wherein Z$_1$ is (CH$_2$)$_3$—(CH$_2$)$_g$—CF$_2$—.

12. A compound according to claim 2, wherein Z$_1$ is —CH$_2$—O—CH$_2$—(CH$_2$)$_g$—CH$_2$—.

13. A compound according to claim 2, wherein Z$_1$ is —(m—Ph)—CH$_2$—(CH$_2$)$_g$—.

14. A compound according to claim 2, wherein Z$_1$ is —(m—Ph)—O—(CH$_2$)$_g$—.

15. A compound according to claim 2, wherein Z$_1$ is cis—CH=CH—CH$_2$—(CH$_2$)$_g$—CH$_2$—.

16. A compound according to claim 10, wherein R$_7$ is —O—(PhI).

17. A compound according to claim 10, wherein R$_7$ is —(CH$_2$)$_m$—(PhI).

18. A compound according to claim 10, wherein R$_7$ is —(CH$_2$)$_m$—CH$_3$.

19. A compound according to claim 13, wherein g is 3.

20. A compound according to claim 13, wherein g is one.

21. A compound according to claim 15, wherein at least one of R$_3$ and R$_4$ is methyl.

22. A compound according to claim 16, wherein R$_3$ and R$_4$ are both methyl.

23. A compound according to claim 15, wherein at least one of R$_3$ and R$_4$ is fluoro.

24. A compound according to claim 18, wherein R$_3$ and R$_4$ are both fluoro.

25. A compound according to claim 15, wherein R$_3$ and R$_4$ are both hydrogen.

26. A compound of claim 1 wherein X$_1$ is —CO$_2$H or —CO$_2$—CH$_3$, Z$_1$ is cis—CH=CH—CH$_2$CH$_2$CH$_2$—, R$_3$ and R$_4$ are hydrogen, and R$_7$ is —(CH$_3$)$_3$CH$_3$.

27. A compound of the formula II or III,

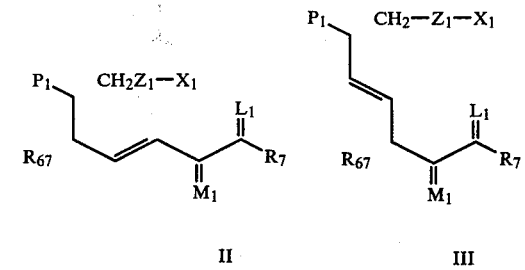

wherein P$_1$ is —C(OH)(H)—CH$_2$—C(H)=CH$_2$;
wherein R$_{67}$ is hydroxy, chloro, bromo, or fluoro;
wherein X$_1$ is —CO$_2$R$_1$, wherein R$_1$ is hydrogen, alkyl of from one to 12 carbon atoms, cycloalkyl of 3 to 10 carbon atoms, aralkyl of from 7 to 12 carbon atoms, phenyl, phenyl substituted by one, 2 or 3 chloro or one, 2 or 3 alkyl, or phenyl substituted in the para position by
  (i) NHC(O)R$_{25}$,
  (ii) —O—C(O)R$_{26}$,
  (iii) —CO$_2$R$_1$,
  (iv) —O—C(O)—(p—Ph)—R$_{27}$, wherein p—Ph is 1,4-phenylene, or
  (v) —CH=N—NH—C(O)—NH$_2$,
wherein R$_{25}$ is methyl, phenyl, acetamidophenyl, benzoylamidophenyl, or NH$_2$; wherein R$_{26}$ is methyl, phenyl, NH$_2$, or methoxy; wherein R$_{27}$ is hydrogen, acetamido, benzoylamido; or R$_1$ can be a pharmacologically acceptable cation;
wherein Z$_1$ is
  (a) cis—CH=CH—CH$_2$(CH$_2$)$_g$—CH$_2$—;
  (b) trans—CH=CH—CH$_2$(CH$_2$)$_g$—CH$_2$—;
  (c) trans—CH=CH—CH$_2$(CH$_2$)$_g$—CH$_2$—;
  (d) cis—CH$_2$—CH=CH—(CH$_2$)$_g$—CH$_2$—;
  (e) trans—CH$_2$—CH=CH—(CH$_2$)$_g$—CH$_2$—; or
  (f) —(CH$_2$)$_3$—(CH$_2$)$_g$—CH$_2$—;
wherein g is one, 2, or 3;
wherein L$_1$ is α—R$_3$:β—R$_4$ or β—R$_3$:α—R$_4$ or a mixture of the two, wherein R$_3$ and R$_4$ are the same or different and are hydrogen, methyl, or fluoro, with the proviso that when R$_3$ is fluoro R$_4$ is fluoro and when R$_4$ is fluoro R$_3$ is fluoro;
wherein R$_7$ is
  (a) —(CH$_2$)$_m$—CH$_3$;
  (b) O—(Ph—s); or
  (c) —(CH$_2$)$_n$(Ph—s); wherein (Ph—s) is phenyl or phenyl substituted by zero, one, 2, or 3 chloro, fluoro, trifluoromethyl, alkyl of from one to 3 carbon atoms, or alkoxy of from one to 3 carbon atoms, with the proviso that not more than two phenyl substituents are other than alkyl, m is one, 2, 3, 4, or 5, and n is zero, one, 2, 3, or 4; and
wherein M$_1$ is α-hydroxy:β-methyl or α-hydroxy:β-hydrogen.

* * * * *

UNITED STATES PATENT OFFICE
CERTIFICATE OF CORRECTION

Patent No. 4,352,760      Dated 5 October 1982

Inventor(s) Kirk M. Maxey

It is certified that error appears in the above-identified patent and that said Letters Patent are hereby corrected as shown below:

Cover Page, line 1, "ORGANIC COMPOUNDS SUBSTITUTED" should read
     -- SUBSTITUTED --.
Column 1, line 1, "ORGANIC COMPOUNDS SUBSTITUTED" should read
     -- SUBSTITUTED --.
Column 7, line 12, "αβ-" should read -- α,β- --. (o-, m-, or p-)
Column 9, line 16, "o-, m-, or p-)" should read --
Column 9, line 27, "α13OH:β-H" should read -- α-OH:β-H --.
Column 9, line 51, "range of 0.5" should read -- range of 0.05 --.
Column 10, line 32, "to the preferred" should read -- to the perfused --.
Column 12, line 26, "Terbutyldimethylsilyl" should read -- Tert-butyldimethyl-
     silyl --.
Column 12, line 39, "3,87,083; 4,00,263;" should read -- 3,987,083;
     4,008,263; --.
Column 15, line 63, ", 139.96, 139.27, 138.56," should read -- , $\underline{139.96}$,
     139.27, $\underline{138.56}$, --.
Column 15, line 65, ", 131.51, 131.35, 130.82, 130.66, 130.34," should read
     -- , $\underline{131.51}$, $\underline{131.35}$, 130.82, 130.66, $\underline{130.34}$, --.
Column 15, line 64, ", 137.50, " should read -- , $\underline{137.50}$, --.
Column 15, line 66, ", 78.54," should read -- , $\underline{78.54}$, --.
Column 15, line 67, ", 29.76," should read --,$\underline{29.76}$, --.
Column 15, line 68, ", 29.62," should read --,$\underline{29.62}$, --.
Column 16, line 16, "cis-CH=CH$_2$CH$_2$-, should read -- cis-CH=CH$_2$CH$_2$CH$_2$-, --.
Column 17, line 45, ", 33.18," should read -- , $\underline{33.18}$, --.
Column 19, line 9, that portion of the formula should appear as follows:

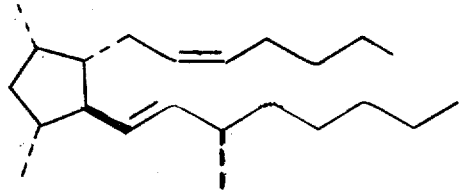

UNITED STATES PATENT OFFICE
CERTIFICATE OF CORRECTION

Patent No. 4,352,760  Dated 5 October 1982

Inventor(s) Kirk M. Maxey

It is certified that error appears in the above-identified patent and that said Letters Patent are hereby corrected as shown below:

Column 20, line 13, that portion of the formula should appear as follows:

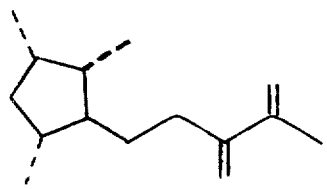

Column 24, formulas II and III, those portions of the formulae should appear as follows:

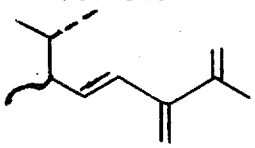   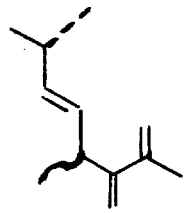

II   III

Signed and Sealed this

Fifth Day of April 1983

[SEAL]

Attest:

GERALD J. MOSSINGHOFF

Attesting Officer   Commissioner of Patents and Trademarks